(12) United States Patent
Waldmann et al.

(10) Patent No.: US 9,752,931 B2
(45) Date of Patent: Sep. 5, 2017

(54) SPECTROMETER WITH MULTIPLE FABRY-PEROT FILTERS FOR GAS ANALYSIS

(71) Applicant: SICK AG, Waldkirch (DE)

(72) Inventors: Torsten Waldmann, Waldkirch (DE); Rolf Disch, Waldkirch (DE)

(73) Assignee: SICK AG, Waldkirch (DE)

( * ) Notice: Subject to any disclaimer, the term of this patent is extended or adjusted under 35 U.S.C. 154(b) by 105 days.

(21) Appl. No.: 14/488,608

(22) Filed: Sep. 17, 2014

(65) Prior Publication Data

US 2015/0092194 A1   Apr. 2, 2015

(30) Foreign Application Priority Data

Oct. 2, 2013   (EP) ..................... 13187159

(51) Int. Cl.

| | |
|---|---|
| *G01J 3/02* | (2006.01) |
| *G01N 33/00* | (2006.01) |
| *G01N 21/3504* | (2014.01) |
| *G01J 3/12* | (2006.01) |
| *G01J 3/26* | (2006.01) |
| *G01J 3/433* | (2006.01) |

(52) U.S. Cl.
CPC ........... *G01J 3/0205* (2013.01); *G01J 3/0235* (2013.01); *G01J 3/12* (2013.01); *G01J 3/26* (2013.01); *G01J 3/433* (2013.01); *G01N 21/3504* (2013.01); *G01N 33/0062* (2013.01); *G01J 2003/1282* (2013.01)

(58) Field of Classification Search
CPC .. G01J 3/0205; G01J 3/433; G01J 3/26; G01J 3/0235; G01J 3/12; G01J 2003/1282; G01N 21/3504; G01N 33/0062
See application file for complete search history.

(56) References Cited

U.S. PATENT DOCUMENTS

| | | | | |
|---|---|---|---|---|
| 3,373,651 | A * | 3/1968 | Mack .................. | G01J 3/26 356/454 |
| 3,519,355 | A * | 7/1970 | Schools ................ | G02B 5/203 356/454 |
| 3,729,261 | A * | 4/1973 | Sandercock ............ | G01J 3/26 356/454 |

(Continued)

FOREIGN PATENT DOCUMENTS

EP      0543578 A1    5/1993

*Primary Examiner* — Hwa Lee
(74) *Attorney, Agent, or Firm* — Nath, Goldberg & Meyer; Jerald L. Meyer (57) ABSTRACT

A spectrometer (10) for gas analysis is provided, the spectrometer comprising a measurement cell (28) having a gas to be investigated, a light source (12) for the transmission of light (14) into the measurement cell (28) on a light path (16), a filter arrangement (22) having a Fabry-Perot filter (24*a-c*) in the light path (16), in order to set frequency properties of the light (14) by means of a transmission spectrum of the filter arrangement (22), as well as a detector (36, 38) which measures the absorption of the light (14) by the gas (30) in the measurement cell (28). In this connection the filter arrangement (22) has a plurality of Fabry-Perot filters (24*a-c*) arranged behind one another in the light path (14) and a control unit (44) for the filter arrangement (22) is provided in order to change the transmission spectrum by setting at least one of the Fabry-Perot filters (24*a-c*).

18 Claims, 7 Drawing Sheets

(56) References Cited

U.S. PATENT DOCUMENTS

| | | | | | |
|---|---|---|---|---|---|
| 3,853,404 | A | * | 12/1974 | Barrett | G01J 3/44 356/301 |
| 3,984,190 | A | * | 10/1976 | Barrett | G01J 3/26 356/301 |
| 3,999,854 | A | * | 12/1976 | Barrett | G01J 3/44 356/301 |
| 4,014,614 | A | * | 3/1977 | Sandercock | G01J 3/26 356/454 |
| 4,225,236 | A | * | 9/1980 | Sandercock | G01J 3/26 356/454 |
| 4,525,067 | A | * | 6/1985 | Hernandez | G01J 3/26 356/454 |
| 4,998,017 | A | * | 3/1991 | Ryan | G01J 3/26 250/343 |
| 5,357,340 | A | * | 10/1994 | Zochbauer | G01J 3/26 356/454 |
| RE35,355 | E | * | 10/1996 | Ryan | G01J 3/26 250/343 |
| 5,606,419 | A | * | 2/1997 | Foosnæs | G01J 3/26 356/419 |

* cited by examiner

Time [a.u.] ; controll parameter [a.u.]

SPECTROMETER WITH MULTIPLE FABRY-PEROT FILTERS FOR GAS ANALYSIS

The invention relates to a spectrometer and to a method for the spectrometric gas analysis in accordance with the preamble of the independent claim of the respective category.

Different methods of infrared spectroscopy are known in order to measure the concentration of individual components of a gas mixture. They are all based on the basic principle of irradiating infrared test light into a measurement cell including the gas to be investigated. In this connection the gases show a characteristic absorption at frequencies which correspond to the spectral lines of its molecules. This absorption changes the properties of the incident light which can be detected and evaluated in different ways.

The Fourier transformation spectroscopy (FTIR) is based on an interferometer and the calculation of an interferogram obtained thereby into a spectrum by means of Fourier transformation. However, such systems are intensive in cost. Grid spectrographs generate a spectrum by a diffraction at the gap, however, lead to a signal weak in intensity. Having regard to the non-dispersive infrared spectroscopy (NDIR) an optical band pass filter is arranged in front of the detector which selectively permits light corresponding to one of the spectral lines to be investigated to pass. This relatively simple method is thus inflexible, as an optical band pass filter has to be provided for each gas component to be detected.

In order to also be able to detect weak signals lock-in methods are used. The transmission light is thus pulsed with a known modulation frequency and the receiver selects the measurement signal by means of the modulation frequency in order to suppress interference in different frequency regions by means of analog mixing processes or digital evaluation. The modulation of the transmission light is commonly generated by pulsed light sources or by mechanical choppers arranged downstream thereof. Both are unsatisfactory, as pulsed infrared radiators only permit small modulation frequencies and a mechanical chopper is susceptible and inflexible, needs to be stabilized and requires a large amount of construction space.

In the not yet published European patent application having the file reference 13156530.1 it is suggested to change the wavelength band of the light irradiated into the measurement cell by means of a tunable Fabry-Pérot filter and to scan this spectrum in this way. A Fabry-Pérot filter is an optical resonator which is formed by two part transparent mirrors. By means of constructive and destructive interference only those wavelengths are transmitted which correspond to the resonance condition. Correspondingly a first transmission maximum arises at the resonance frequency and a further transmission maximum of higher order arises at the higher order waves, whereas the intermediate frequencies are nearly completely excluded. The spacing between the transmission maximum is referred to as a free spectral range.

If one varies the mirror spacing and/or the air gap between the mirrors then the transmission maxima are simultaneously influenced with respect to their width and their mutual spacing. A fine needle of a transmission maximum for this reason brings about a reduced free spectral range, whereas vice versa a larger free spectral range can only be achieved at the price of transmission maximas of large full width at half maximum. This characterization of Fabry-Pérot's filter is reflected in the so-called finesse which defines the ratio of the free spectral range with respect to the full width at half maximum.

For these reasons a plurality of absorption lines of one or more gas components is incident at the pass band of a Fabry-Pérot filter as they lie within the same transmission maximum of a Fabry-Pérot filter with a high full width at half maximum or as the free spectral range of a Fabry-Pérot filter with a reduced full width at half maximum is too small in order to selectively set the Fabry-Pérot filter with respect to an absorption line without the side maxima coinciding with further absorption lines.

The spectral resolution capability achievable by means of a Fabry-Pérot filter is limited for this reason. If one wants to achieve a higher spectral resolution then one commonly makes use of the above-mentioned methods, such as FTIR or grid spectroscopy.

For this reason it is the object of the invention to improve the measurement of a spectrum for gas analysis.

This object is satisfied by a spectrometer and by a method of spectrometric gas analysis in accordance with independent claim of the respective category. In this connection frequency properties are embossed onto light with the aid of a filter arrangement prior to the light being irradiated for spectrometry into a measurement cell having a gas and/or a gas mixture to be investigated. The absorption by means of the gas is then detected and the concentration of the gas components are thus measured. The invention now starts from the basic idea of providing a plurality of Fabry-Pérot filters in the filter arrangement.

Through the setting of at least one of the Fabry-Pérot filters the transmission spectrum of the filter arrangement changes and thus the desired frequency properties of the light can be achieved. This enables, for example, to consecutivelz continuously set or tune the spectrometer with respect to the absorption spectra of different gases of gas mixtures in order to scan a larger wavelength range.

The invention has the advantages of Fabry-Pérot filters which are cost-effective, compact mechanically simple and in this way low in maintenance and robust and which have a high optical throughput. Variable frequency properties of the irradiated light can be set very quickly and flexibly. At the same time, however, through the multiple arrangement of Fabry-Pérot filters, a high spectral resolution is made possible. Since new degrees of freedom of adjustment result which can, for example, be used in order to achieve a low full width at half maximum and a large free spectral range at the same time. This would not be plausible with respect to a single Fabry-Pérot filter due to the direct association of these parameters and limits the common achievability of spectral resolution in a considerable manner.

In order to set a Fabry-Pérot filter in particular its air gap and/or its mirror spacing is changed. Thereby the resonance frequency and as a consequence thereof the transmission spectrum is varied. The Fabry-Pérot filters are for this reason, for example, assembled as electrostatically or as piezoelectrically controlled microsystems (MEMS, Micro Electro Mechanical System). This combines robustness, small construction sizes and short reaction times at least in the millisecond region.

The filter arrangement preferably has three Fabry-Pérot filters. In principle a higher flexibility is already obtained by means of two Fabry-Pérot filters. The more Fabry-Pérot filters are additionally provided in the filter arrangement the more degrees of freedom are obtained. A number of three Fabry-Pérot filters in this connection forms a preferred compromise.

An association of mirror spacings of the Fabry-Pérot filters and of the associated transmission spectra is preferably stored in the control unit. The association is predefined during the manufacture or is taught at the start of a measurment in calibration measurements. By means of the association the control unit can set a desired transmission spectrum of the filter arrangement. At least one Fabry-Pérot filter is involved in the adjustment process, also more or all Fabry-Pérot filters can be involved.

The Fabry-Pérot filters preferably have graduated full widths at half maximum, in particular having regard to three Fabry-Pérot filters respectively a Fabry-Pérot filter with a low full width at half maximum, a Fabry-Pérot filter with a mean full width at half maximum and a Fabry-Pérot filter with a high full width at half maximum is provided. Intuitively a cooperation of the Fabry-Pérot filters is most comprehensible for which the Fabry-Pérot filter of lowest full width at half maximum determines the spectral resolution and the remaining Fabry-Pérot filters ensure that the higher orders of the respectively finer resolving Fabry-Pérot filters are masked out in a graduated manner. However, in many situations also other combinations exist in order to achieve a desired transmission spectrum.

The transmission spectrum preferably has a narrow band maximum at a predefined frequency. Additionally, even more preferably, frequency portions outside of this maximum are substantially suppressed. Thus the filter arrangement ensures that only light of a certain frequency arrives in the measurement cell. Thus, a spectrum can be scanned with a plurality of individual measurements under an intermittent displacement of the frequency of the maximum.

The control unit is preferably configured for the purpose of varying the transmission spectrum of the filter arrangement cyclically in such a way that the amplitude of the maximum is modulated. In this way, the filter arrangement simultaneously forms an optical pulse shape. This is in particular achieved by a subsequent tuned cyclic displacement of the Fabry-Pérot filters.

For example the maximum of the Fabry-Pérot filter having the largest full width at half maximum is cyclically displaced in such way that the position of this maximum coincides to a different degree with the maxima of the other Fabry-Pérot filters. Thereby a similar effect is achieved as by means of an aperture which alternatively lets light pass or blocks light. However, also numerous other positions of the Fabry-Pérot filters exist in which their transmission maxima are hardly or not at all superimposed such that the light is practically blocked and the intermediate steps can be controlled in order to also achieve a pure bright-dark modulation. The plurality of Fabry-Pérot filters thus enables, in a double function, to scan the spectrum with a high resolution and simultaneously to achieve a modulation of the light intensity of the light incident into the measurement cell without additional elements.

The amplitude is preferably modulated with a predefinable function, in particular a delta pulse, a sinusoidal pulse or an exponentially growing and then abruptly falling off pulse. A delta pulse corresponds to a pure bright-dark modulation. A sinusoidal pulse and/or a cosinusoidal pulse are supported particularly well by electronic and digital lock-in methods. The function can be selected in a nearly arbitrary manner in that the filter arrangement is adjusted in intermediate positions which lead to different dampings of the transmission maximum. One of numerous examples is a modulation with pulses, which look similar to shark fins, this means that they initially grow comparatively slowly in an exponential manner towards their brightness maximum and then abruptly fall off into the dark state. Such a modulation forms an example simple to calculate.

The control unit is preferably configured to vary the transmission spectrum in accordance with a scanning scheme, following which a transmission spectrum is respectively generated with a maximum at a scanning frequency, the amplitude of the maximum is modulated over a plurality of cycles at the scanning frequency and the scanning frequency is then systematically changed. With such a scanning schemes the spectrum is respectively scanned with a pulse sequence at different frequencies.

A signal of the detector is preferably evaluated with a lock-in method by means of the known modulation. This is the principle of the lock-in amplifier which is set in an analog or digital manner with respect to the known modulation frequency and thereby achieves a significantly improved signal-to-noise ratio. The required modulation of the light preferably takes place as just described in the filter arrangement itself, however, principally also an additional optical pulse shaper or a pulsed light source is plausible.

Preferably an additional optical band pass filter is provided in the light path in order to mask out maxima of higher orders of at least one of the Fabry-Pérot filters preferably of the Fabry-Pérot filter having the highest free spectral range. The Fabry-Pérot filters with the larger free spectral range practically already satisfy this function within the filter arrangement, in that they suppress higher orders of Fabry-Pérot filters of a smaller free spectral range. However, this is not necessarily sufficient in order to exclude all non-desired spectral portions and for this reason the optical band pass filter limits the frequency band totally to a region of interest which is preferably as large as the resultant free spectral range of the filter arrangement. Such a band pass filter can also be integrated into the optical path in a transmission or reception optics. Alternatively, the light source or the detector are of sufficient narrow band design in order to exclude remaining higher orders of the filter arrangement on its own.

The measurement cell is preferably a photo acoustic cell. Reduced gas concentrations for short absorption paths can also be measured therein and the measurement cell has a high dynamic range. The photo acoustic measurement cell measures pressure changes which are generated by the heating of the gas for radiation absorption of the light incident in the measurement cell. These pressure changes are acoustically measured, for example with a microphone or a pressure sensor. Preferably, modulated light hereby ensures a sufficient change of state.

In a preferred embodiment of the photo acoustic measurement cell this has a cantilever, for example in the form of a silicon membrane and an interferometer for the optical measurement of the deflection of the cantilever by means of interferometry. The absorption ensures a very quick heating and in this way an impulse-like pressure change of the gas for a sufficient conformity of the frequency properties of the incident light and of the absorption spectrum of a gas component. The thereby effected deflection of the cantilever is then evaluated interferometrically.

Preferably, a calibration unit is provided which can be introduced into a light path and which can be removed from the light path and that has an interference filter with a known reference frequency or has a gas cuvette having a reference gas. Although the resonance properties of a Fabry-Pérot filter and in this way its transmission spectrum can be predicted very well in theory, in practice tolerances arise when the control unit sets a certain mirror spacing. This is compensated in a calibration by means of a comparison with the known reference frequency and thus the respective band pass wavelength and/or its intensity can be set in a particularly exact manner. The reference gas can also be introduced into the measurement cell. On use of a reference gas one has to consider the temperature and pressure stable conditions as is normal.

The calibration unit preferably has a moveable carriage or a filter wheel. Thereby, the calibration can be carried out particularly simply and if required can be repeated. Respectively a plurality of reference gases and/or interference filters can be provided in order to calibrate a plurality of calibration points.

At least one Fabry-Pérot filter is mounted preferably in such a way that it can be removed from the light path and can be reintroduced into the light path. A moveable carriage can also serve for this purpose. In this way, the Fabry-Pérot filters can be calibrated not only in common as a filter arrangement, but individually or also in a group. This simplifies the calibration process and leads to more exact results.

The method in accordance with the invention can be furthered in a similar manner and in this connection shows similar advantages. Such advantageous features are mentioned by way of example, but not conclusively in the dependent claims relating to the independent claims.

The invention will be described in detail in the following also with respect to further features and advantages by means of embodiments and with reference to the submitted drawing. The images of the drawing show in:

FIG. 2b a common transmission spectrum of the three Fabry-Pérot filters arranged behind one another in accordance with FIG. 2a;

FIG. 4b a common transmission spectrum like FIG. 2b which has three Fabry-Pérot filters arranged behind one another according to FIG. 4a;

Figure 1:
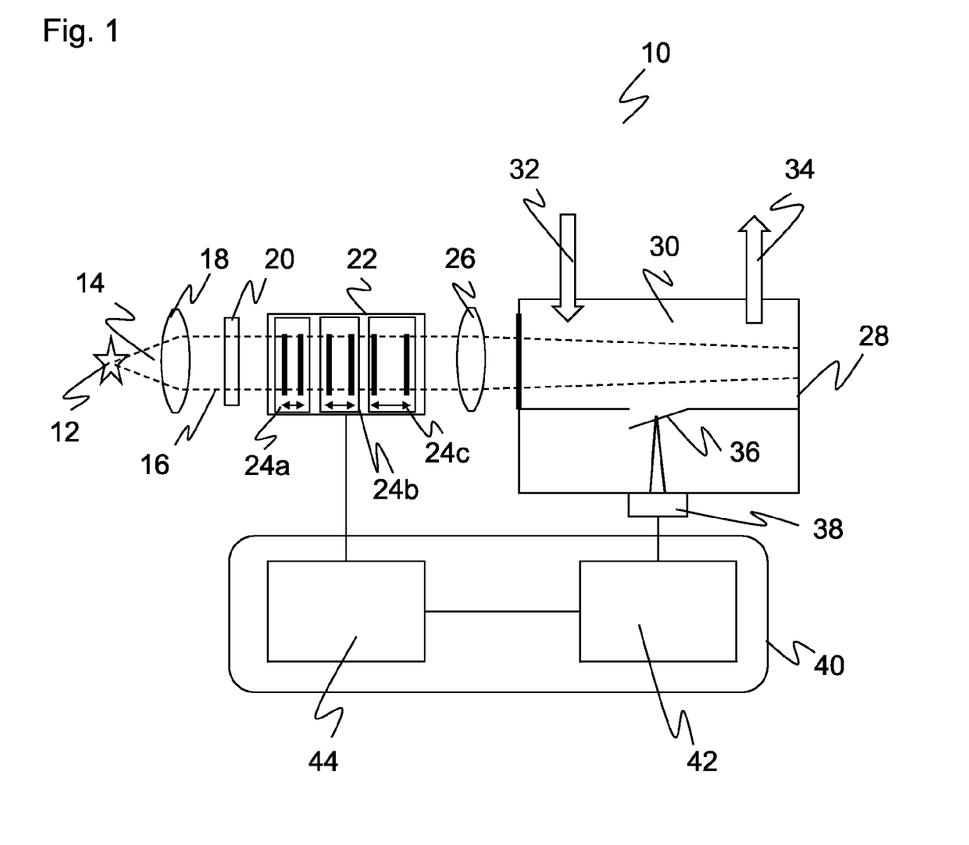
FIG. 1 an overview illustration of a spectrometer.

FIG. 1 shows an overview illustration of a spectrometer 10 for the determination of gas components by means of an absorption measurement. A light source 12 transmits light 14, which on its light path 16 passes a first optics 18 or a band pass filter 20, a filter arrangement 22 having a plurality of Fabry-Pérot filters 24a-c and a second optics 26, is irradiated into a measurement cell 28. In the measurement cell 28 a gas 30 to be investigated and/or a gas mixture is present for which a gas inlet and a gas outlet 34 are provided as symbolized by the arrows.

A detector is present in the measure cell 28 which in the present instance is configured as a cantilever 36 having a (laser-)interferometer 38 for the determination of the deflection of the cantilever 36. A control and evaluation unit 40 has a measurement unit 42 for the evaluation of the signals of the interferometer 38, a control unit 44 for the setting of the filter arrangement 22 and the remaining required control and evaluation functionality. The division of the control and evaluation unit 40 only serves the clear explanation, however, also a different division with respect to one or more physical control and evaluation units is possible which exchange data and state parameters amongst one another.

The light source 12 is preferably a broad band infrared radiator. In this way, the typical frequency range of spectral lines of the molecules of the gases to be investigated is covered. The light 12 is bunched by the first optics 18, wherein the illustrated lens is only represented for one or more suitable optical elements for beam forming and beam guidance. The band pass filter 20 cuts a coarse range out of the broader frequency band of the light source 12 within which its absorption bands of the gas to be investigated lie. For example, the gas component CO, NO, $SO_2$, $NO_2$, $N_2O$, $CO_2$ and $H_2O$ can be measured in the frequency band of 4.3 µm to 7.4 µm and numerous hydrocarbons can be measured in the frequency band of 3 µm to 3.8 µm. Frequencies outside such ranges or frequencies with spectral lines of gases which cannot be measured with a certain spectrometer can, for this reason, be suppressed from the start with the aid of the band pass filter 20. The band pass filter 20 can also be present at a different position in the light path 16 than illustrated or can be integrated into one of the optics 18, 26. Alternatively, a slightly more narrow band light source 12 can be used, for example, an LED and one can omit the band pass filter 20. Also the filter arrangement 22 itself can, within certain boundaries, take over the function of the band pass filter 20.

The transmission spectrum of the filter arrangement 22 can be predefined in a desired manner by the setting of the Fabry-Pérot filters 24a-c, which are considered in more detail in the following, such that the light 14 has certain frequency properties after passing through the filter arrangement 22. Preferably, only a narrow transmission maximum remains at a predefined frequency which is then displaced in a plurality of individual measurements by means of the frequency regions of interest. Alternatively, the transmission maximum is targetly brought into conformance with a known spectral line in order to measure the associated gas components. The second optics 26 guides the filtered light 14 into the measurement cell 28, wherein, as is to be understood already for the first optics 18, the illustration with respect to a simple single lens is to be understood purely by way of example. Further optical elements can also be provided within the filter arrangement 22, in particular between the Fabry-Pérot filters 24a-c.

Only when the frequency properties of the light incident into the measurement cell 28 coincide with one or more spectral lines of the molecules of the gas 30, is light of a corresponding frequency absorbed. This then leads to a heating of the gas 30 and in this way to a pressure increase in the measurement cell 28, which in turn deflects the cantilever 36 in a proportional manner with respect to the concentration of the related gas component or gas components. The interferometer 38 recognizes this deflection to a high precision. The measurement with a photo acoustic cell 28 of this manner of construction is particularly accurate for this reason. However, also a different photo acoustic measurement, for example, by means of a microphone or a pressure sensor, as well as a completely different manner of detection, for example by means of an infrared detector can be provided, which measures the light 14 transmitted to the gas 30 and therefrom draws a conclusion with respect to the absorption. In this connection, arrangements with a detector outside of the measurement cell 28 are plausible and the light transmitted through the measurement cell 28 is then deflected by means of a suitable optics onto the detector. Likewise an arrangement, in which the light is reflected behind the measurement cell 28 and is then registered following a double transmission through the measurement cell 28 in a detector is likewise possible, for example, by means of a beam divider arrangement between light source 12 and the detector.

With reference to the FIGS. 2 to 7 the manner of function of the filter arrangement 22 will now be explained in detail. The control unit 44 is in a position to change parameters of at least one of the Fabry-Pérot filters 24a-c, in particular the air gap between its two semipermeable mirrors and in this way the resonance frequency. This can for example be implemented by an electrostatic or a piezoelectric control of Fabry-Pérot filters configured as MEMS having short reaction times without macroscopic movements. Thereby, the transmission spectrum of the filter arrangement 22 can be predefined.

Figure 2A:
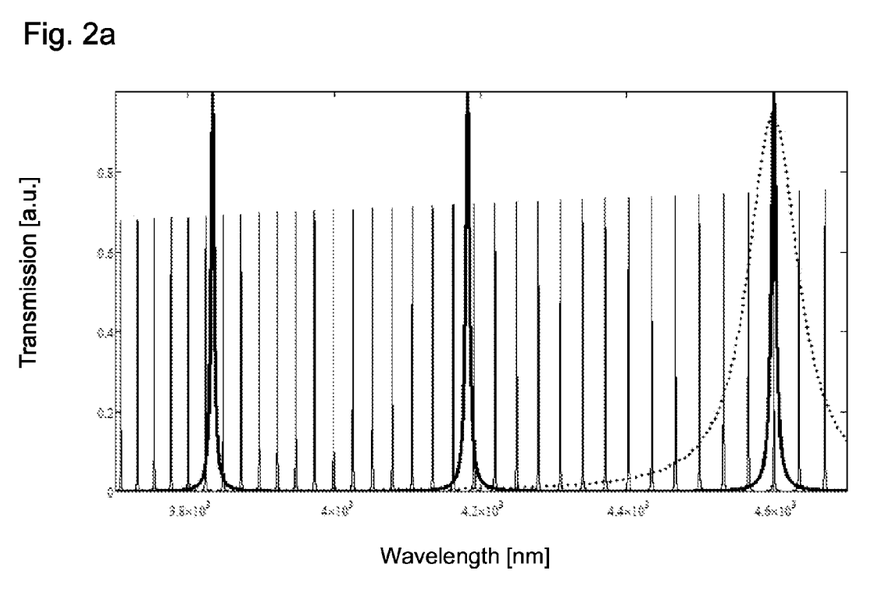
FIG. 2a transmission spectra of three different Fabry-Pérot filters.

FIG. 2a shows an example of three transmission spectra of three Fabry-Pérot filters 24a-c. A Fabry-Pérot filter 24a of smallest full width at half maximum generates the needle-like transmission maxima which are illustrated by a thin line and which lie close to one another and next to one another. A further Fabry-Pérot filter 22b at a mean full width at half maximum has three transmission maxima illustrated with a fat line in the illustrated frequency section. A third Fabry-Pérot filter 24c only shows one relatively wide transmission maximum ilustrated by a dotted line in the illustrated frequency section. This also illustrates the dependency of the full width at half maximum and of the density of the transmission maxima described in the introduction, this means the free spectral range: the more narrow a transmission maximum is and in this way the more suitable a transmission maximum is for higher spectral resolutions of a transmission maximum, the closer also the next transmission maximum of higher order lies. None of the Fabry-Pérot filters 24a-c is individually suitable for a high resolution spectrometer for this reason, since the light cannot be limited in a targeted manner to a certain narrow frequency range.

Figure 2B:
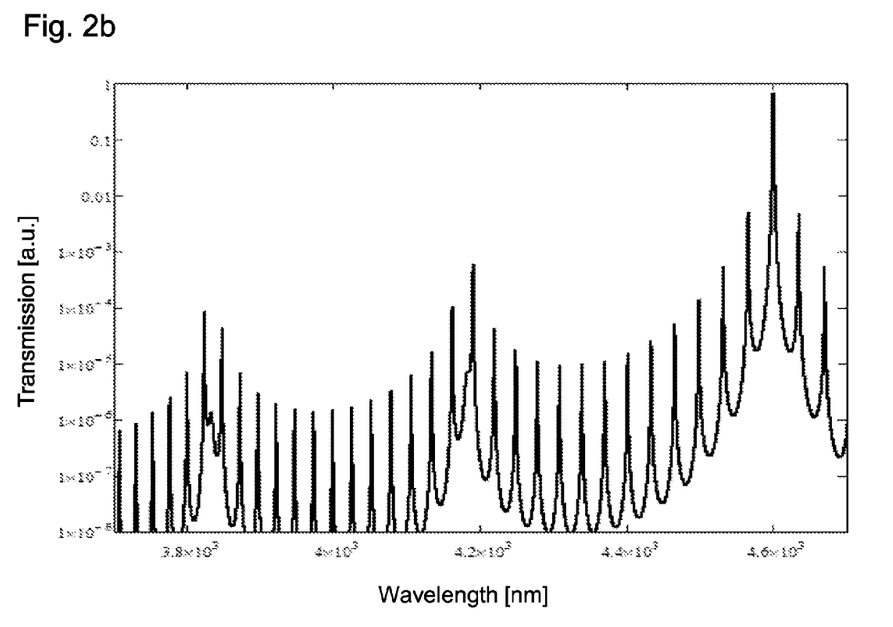

This is achieved by the arrangement of three Fabry-Pérot filters 24a-c arranged behind one another. FIG. 2b shows the associated common transmission spectrum, this finally means the point-wise multiplication of the three transmission spectra of FIG. 2a. A significantly pronounced transmission maximum results at the position where, in FIG. 2a, the transmission maximum of all three Fabry-Pérot filters 24a-c are superimposed on one another. The remaining transmission maximum can still be recognized, however, are very significantly suppressed, as a Fabry-Pérot filter 24a-c having a larger free spectral range respectively suppresses the transmission maxima of higher orders of a Fabry-Pérot filter with a narrow full width at half maximum. In this connection also the logarithmic representation of the FIG. 2b has to be considered. Also with respect to the Fabry-Pérot filter 24c having the widest transmission maximum, the free spectral range is not necessarily sufficient in order to cover the overall bandwidth of the light source 12, for which reason the band pass filter 20 additionally optionally reduces the frequency range, for example, to the section shown in the Figures or totally to a pass band which is as large as the free spectral range of one or more of the Fabry-Pérot filters 24a-c.

Figure 3:
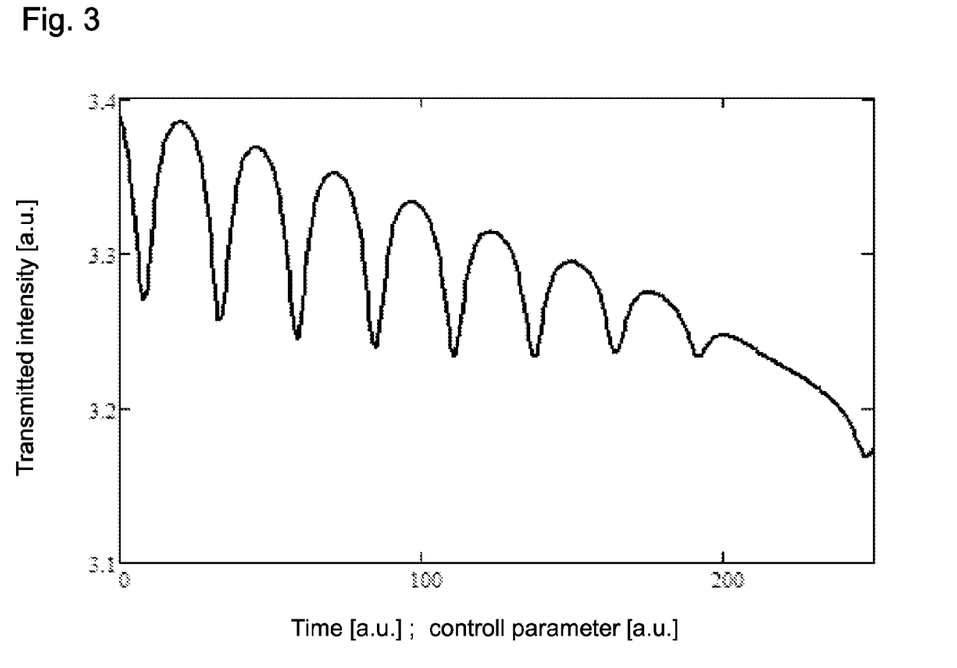
FIG. 3 an exemplary spectral scanning of CO.

Through a successive change of the central wavelength of the region shown in FIG. 2b, the absorption spectrum of the gas 30 can now be scanned. FIG. 3 by way of example shows the result of the successive scanning of the spectrum of CO.

This high resolution spectrometry can now be expanded with the like assembly by a modulation in order to enable a lock-in method in the detection. In the specifically shown embodiment having a photo acoustic measurement cell 28, the cantilever 24 is periodically deflected thereby and its oscillation is interferometrically evaluated. However, lock-in methods can also, for example, be used for the amplification of the signals of an infrared detector.

Figure 4A:
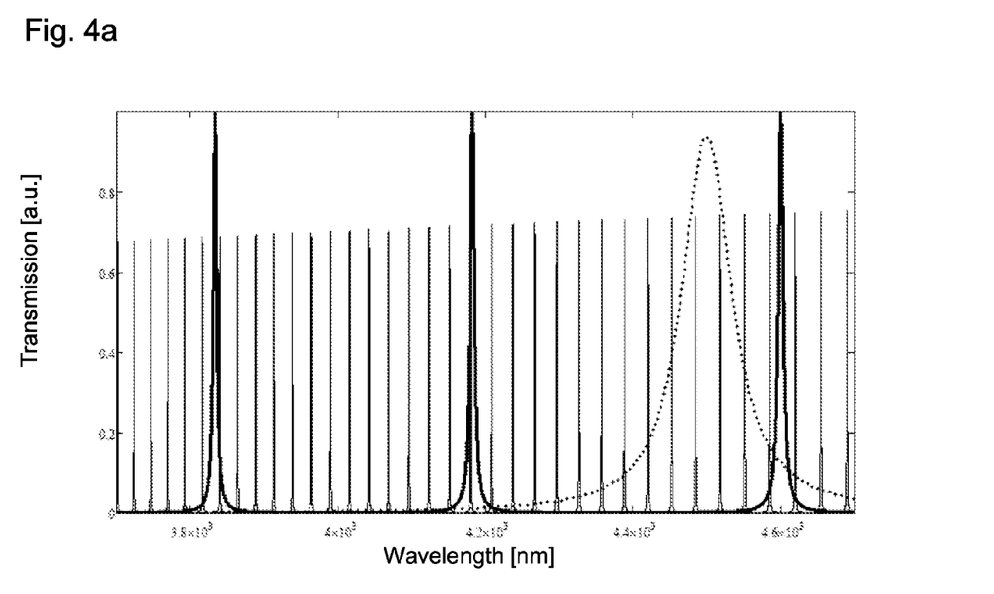
FIG. 4a transmission spectra like FIG. 2a of three different Fabry-Pérot filters, however with mutual tunability and in this way the transmission maxima have a mutual displacement.
Figure 4B:
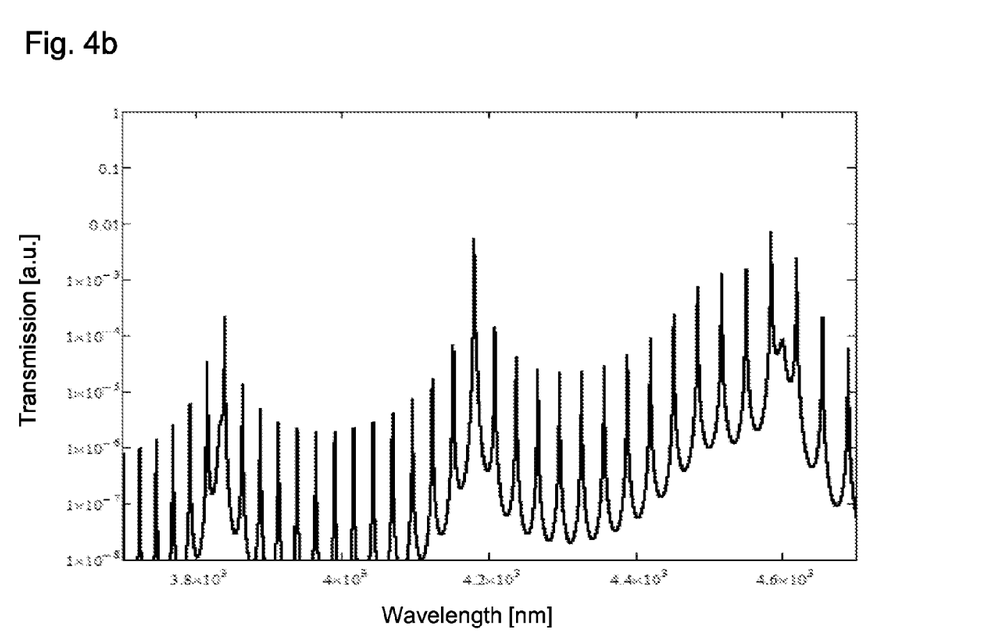

The filter arrangement 22, in a double function itself and in this way without additional components, is in the position to generate the required modulation. For this purpose, the Fabry-Pérot filters 24a-c are periodically out of tune with respect to one another and in this way specifically leave the shown bright stage shown in FIG. 2 for an intermittent time. This is illustrated in FIG. 4. FIG. 4a shows an illustration similar to FIG. 2a, wherein, in this instance, the transmission maxima are however displaced with respect to one another, such that they do not superimpose on one another, if possible at no frequency. Having regard to the widest transmission maximum shown with the dotted line this can be recognized immediately. However, also with respect to the mean transmission maximum shown with the fat line at 4.6 μm this no longer coincides with a needle-like transmission maximum illustrated with a thin line. If possible, the superposition at 4.2 μm could also be prevented by fine adjustment. In the resultant common transmission spectra in accordance with FIG. 4b the transmission maximum at 4.6 μm is damped by two orders of magnitude. A cyclic change between the settings in accordance with FIG. 2 and FIG. 4 for this reason leads to a bright-dark modulation with two brightness steps per pass band wavelength.

However, not only simple bright-dark modulations, but also selectable modulations variable in time of the transmitted light power are possible. For this purpose a dark state is not directly controlled as shown in FIG. 4, but also intermediate states of various intensity are controlled.

Figure 5A:
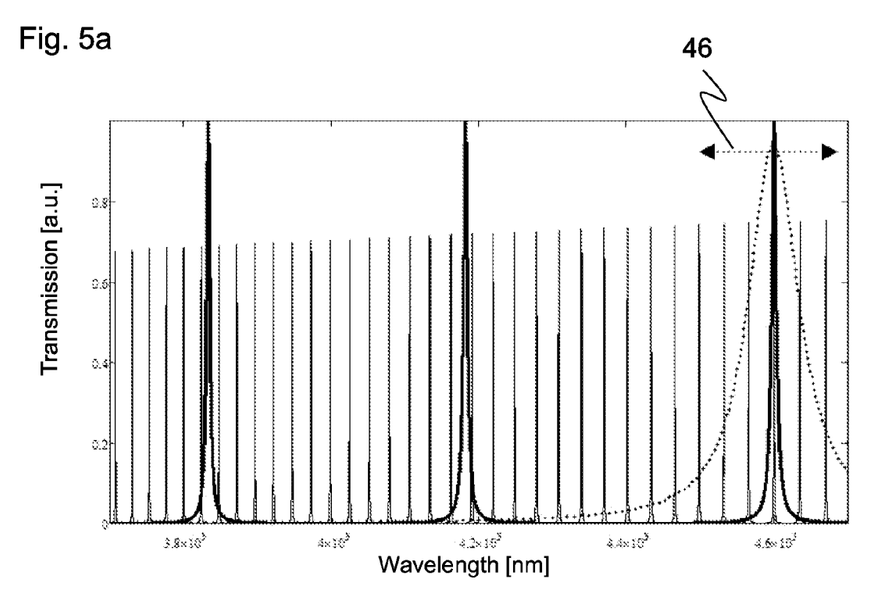
FIG. 5a transmission spectra in accordance with FIG. 2a and FIG. 4a for the illustration of possible changes of setting with respect to the amplitude modulation of the resultant maximum in the common transmission spectrum.

FIG. 5 explains the processes. The illustration of FIG. 5a corresponds substantially to that of the FIG. 2a, however, a modulation scheme is indicated by an arrow 46. This is based on the setting of the air gap of the Fabry-Pérot filter 24c having the largest full width at half maximum and with the largest free spectral range. This is only an example which is particularly intuitively comprehensible, also other combinations of settings of the Fabry-Pérot filters 24a-c would lead to the desired result.

Figure 5B:
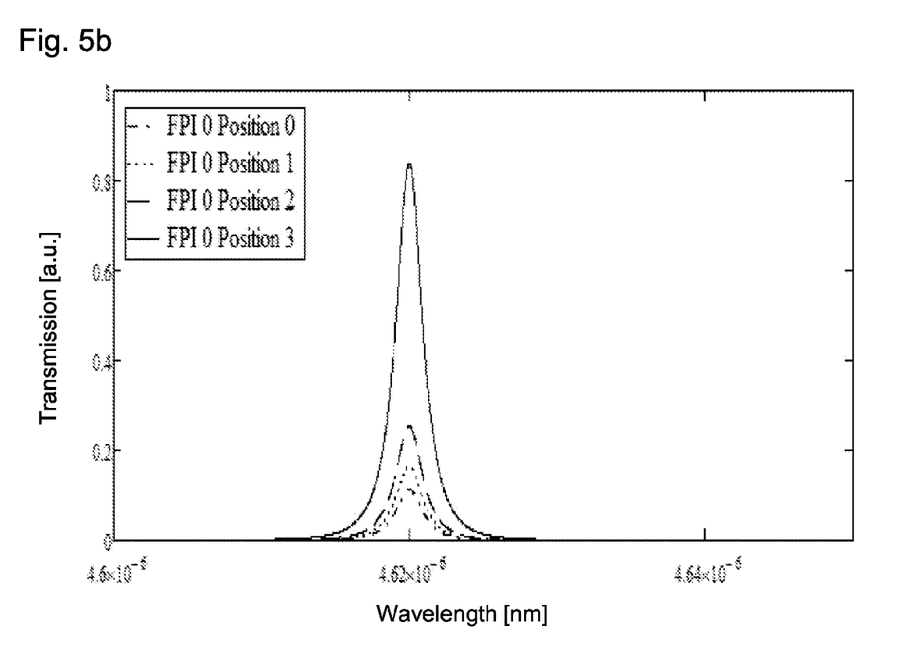
FIG. 5b the maximum of the common transmission spectrum of the three Fabry-Pérot filters arranged behind one another in accordance with FIG. 5a having a plurality of changes of setting.

A different amplitude results in the intermediate states for the common transmission maximums at 4.6 μm. This is shown in FIG. 5b by way of example for four settings of the Fabry-Pérot filters 24c.

Figure 6:
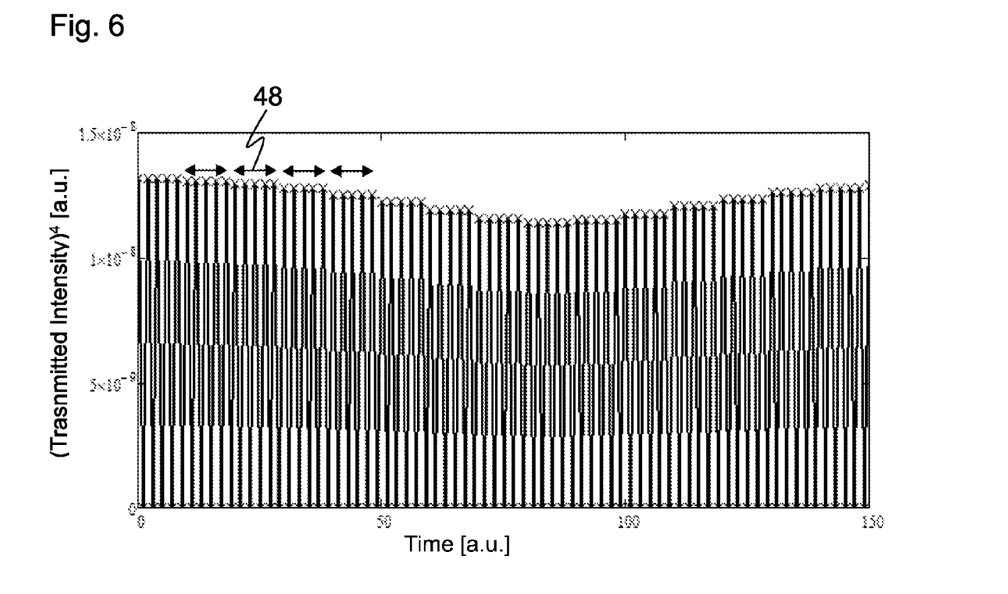
FIG. 6 a scanning scheme for the modulation of the incident light having respectively five bright-dark cycles per set wavelength band.

FIG. 6 shows a section of an exemplary scanning of a CO absorption line having a scanning and modulation scheme. Having regard to each of the set pass band wavelengths respectively five bright-dark cycles are carried out. Respectively ten data points thus correspond to a band pass wavelength. The cycles for four pass bans wavelengths are illustrated by arrows 48.

Figure 7:
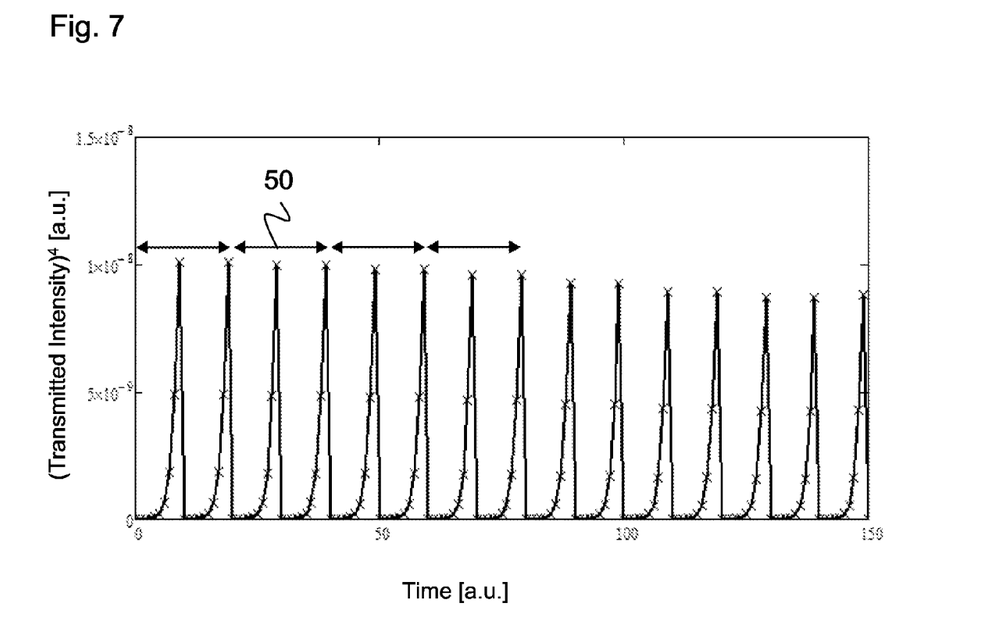
FIG. 7 a further scanning scheme with respect to a modulation of the incident light having two shark fin-like cycles respectively per set wavelength band.

Both the number of the cycles as well as the modulation per cycle can be varied in an arbitrary manner. For this purpose, FIG. 7 shows an extract of a further exemplary scanning of a CO line with a different scanning and modulation scheme. In this instance, respectively two modulation cycles are carried out for each set pass band wavelength, as is illustrated for four cycles by arrows 50. The modulation itself is no simple bright-dark change, but via a plurality of steps, in this instance a total of ten intensity modulations, leads to an exponential growth and a subsequent abrupt falling off ("shark fin"). In an analog manner practically any arbitrary scanning and modulation scheme can be realized.

The filter arrangement 22 is thus in a position to transmit light into a narrow wavelength range in order to successively transmit a successively changing central wavelength into the measurement cell 28, wherein the light can also be modulated if required.

Figure 8:
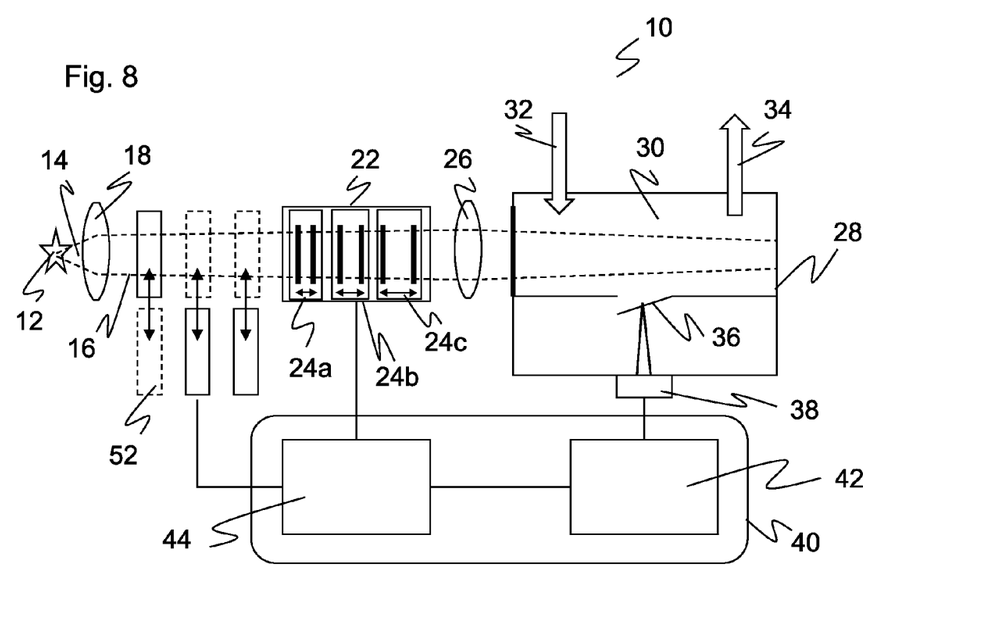
FIG. 8 an overview illustration of a further embodiment of the spectrometer having a variable element that can be introduced into the light pass for the calibration.

The transmission spectrum of a Fabry-Pérot filter 24$a$-$c$ depends on control parameters which are set by the control unit 44. In order to calibrate this, additional elements 52 can be introduced into the light path 16 and/or can be removed therefrom in a further embodiment of the spectrometer 10 in accordance with FIG. 8. In this connection the elements 52 have a known spectrum which is drawn upon as a reference. Two examples of such elements 52 are interference filters of known wavelength dependent transmission or closed reference gas cuvettes of known length and filling having one or more gas components of known concentration. In this connection one has to consider temperature stability and in the case of a reference gas, also pressure stability. On use of the elements 52 and measurement of the spectrum, the transmission spectra including the band pass wavelength and transmission intensity of the Fabry-Pérot filters 24$a$-$c$ are calibrated in dependence on one or more control parameters. The introduction or removal of the elements 52 can be achieved by a filter wheel or by a mechanical moveable carriage. An alternative embodiment provides a narrow band laser light source for the calibration instead of elements 52 in the light path 16.

Figure 9:
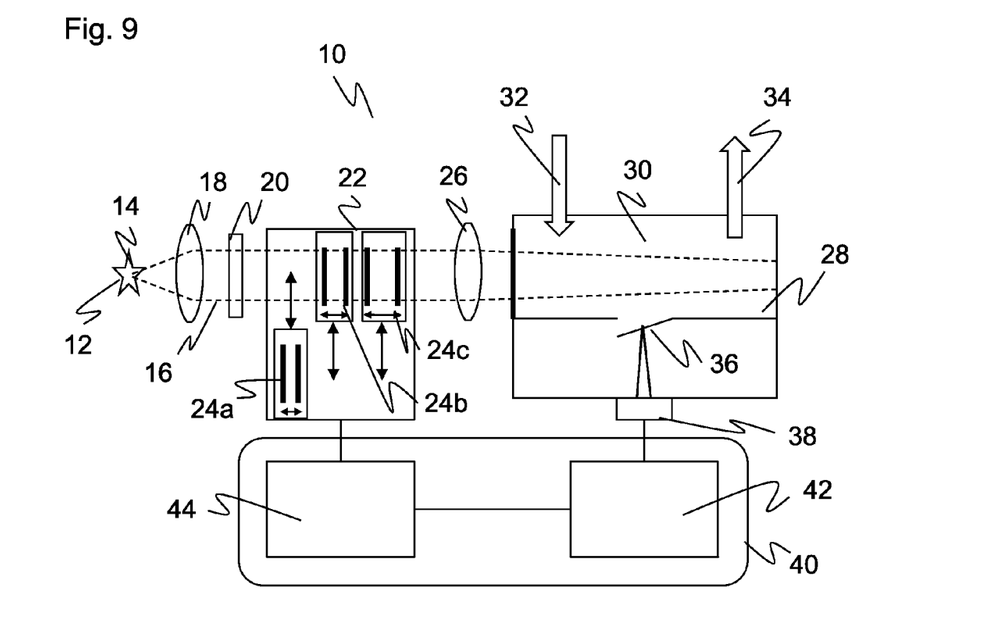
FIG. 9 an overview illustration of a further embodiment of a spectrometer Fabry-Pérot filters selectively removable from the light path.

FIG. 9 shows a further embodiment of the spectrometer 10. In this embodiment the Fabry-Pérot filters 24$a$-$c$ can likewise be removed from and introduced into the light path 16 by means of moveable carriages or the like, individually or in groups. This can also be combined with the embodiment in accordance with FIG. 8. The embodiment in accordance with FIG. 9 permits the calibration of the Fabry-Pérot filters 24$a$-$c$ individually or in groups and not only of the filter arrangement 22 in its totality. This increases the preciseness and simplifies the process.

Having regard to the calibration of the Fabry-Pérot filters 24$a$-$c$ it is also plausible to fill the measurement cell 28 with a calibration or reference gas whose gas components including their concentration is known. Furthermore, it is possible to introduce a detector into the light path 16 for recalibration instead of the measurement cell 28 which measures the intensity in the relevant spectral range and thereby can monitor the setting of the filter arrangement 22 and/or the properties of the overall light path 16.

What is claimed is:

1. A spectrometer for gas analysis, the spectrometer comprising:
   a measurement cell having a gas to be investigated;
   a light source for the transmission of light into the measurement cell on a light path;
   a filter arrangement having a plurality of Fabry-Perot filters arranged behind one another in the light path, in order to set frequency properties of the light by means of a transmission spectrum of the filter arrangement;
   a detector which measures the absorption of the light by the gas in the measurement cell; and
   a control unit for the filter arrangement for changing the transmission spectrum in accordance with a scanning scheme by setting at least one of the Fabry-Perot filters, the scanning scheme providing a respective transmission spectrum having a narrow band maximum at a scanning frequency, modulating the amplitude of the narrow band maximum at the scanning frequency over a plurality of cycles, and systematically varying the scanning frequency in order to successively evaluate a spectrum at different frequencies with a lock-in-method based on the known modulation.

2. The spectrometer in accordance with claim 1, wherein the filter arrangement has three Fabry-Perot filters.

3. The spectrometer in accordance with claim 1, wherein an association of mirror spacings of the Fabry-Perot filters and of associated transmission spectra are stored in the control unit.

4. The spectrometer in accordance with claim 1, wherein the Fabry-Perot filters have graduated full widths at half maximum.

5. The spectrometer in accordance with claim 2, wherein the three Fabry-Perot filters have graduated full widths at half maximum.

6. The spectrometer in accordance with claim 1, wherein the transmission spectrum has a narrow band maximum at a predefined frequency.

7. The spectrometer in accordance with claim 6, wherein the control unit is configured to vary the transmission spectrum of the filter arrangement cyclically in such a way that the amplitude of the maximum is modulated.

8. The spectrometer in accordance with claim 6, wherein the amplitude is modulated with a predefined function.

9. The spectrometer in accordance with claim 7, wherein the predefined function is one of a delta pulse, a sinusoidal pulse and an exponentially growing and then abruptly falling off pulse.

10. The spectrometer in accordance with claim 7, wherein a signal of the detector is evaluated with a Lock-In-method by means of the known modulation.

11. The spectrometer in accordance with claim 1, further comprising an additional optical band pass filter in the light path, in order to mask out maxima of higher orders of at least one of the Fabry-Perot filters.

12. The spectrometer in accordance with claim 11, wherein the optical band pass filter is provided to mask out maxima of higher orders of the Fabry-Perot filter of the highest free spectral range.

13. The spectrometer in accordance with claim 1, wherein the measurement cell is a photo-acoustic measurement cell.

14. The spectrometer in accordance with claim 1, further comprising a calibration unit that can be introduced into and removed from the light path and that has an interference filter with a known reference frequency or has a gas cuvette having a reference gas.

15. The spectrometer in accordance with claim 14, wherein the calibration unit has a moveable carriage or a filter wheel.

16. A spectrometer in accordance with claim 1, wherein at least one of the Fabry-Perot filters is mounted such that it can be removed from the light path and can be reintroduced into the light path.

17. The spectrometer in accordance with claim 2, wherein:
- the first Fabry-Perot filter has a low full width half maximum;
- the second Fabry-Perot filter has a mean full width half maximum; and
- the third Fabry-Perot filter has a high full width half maximum.

18. A method of spectrometric gas analysis, comprising:
- passing a light source through a filter arrangement having a plurality of Fabry-Perot filters arranged behind one another;
- setting the frequency properties of the light by changing the transmission spectrum of the filter arrangement in accordance with a scanning scheme;
- guiding the light into a measurement cell having a gas to be investigated; and
- measuring the absorption of the light by the gas in the measurement cell, wherein the absorption is measured a plurality of times after a respective adjustment of at least one of the plurality of Fabry-Perot filters and is thereby measured a plurality of times with light of different frequency properties, the scanning scheme providing a respective transmission spectrum having a narrow band maximum at a scanning frequency, modulating the amplitude of the narrow band maximum at the scanning frequency over a plurality of cycles, and systematically varying the scanning frequency in order to successively evaluate a spectrum at different frequencies with a lock-in-method based on the known modulation.

\* \* \* \* \*